US00PP20544P2

(12) United States Plant Patent
Guillou

(10) Patent No.: US PP20,544 P2
(45) Date of Patent: Dec. 8, 2009

(54) ***GERANIUM* PLANT NAMED 'FIGRADOL PURPLE'**

(50) Latin Name: *Pelargonium peltatum*
Varietal Denomination: Figradol Purple

(75) Inventor: Maurice Guillou, Saint Malo (FR)

(73) Assignee: Fides B.V., De Lier (NL)

( * ) Notice: Subject to any disclaimer, the term of this patent is extended or adjusted under 35 U.S.C. 154(b) by 0 days.

(21) Appl. No.: 12/229,593

(22) Filed: Aug. 25, 2008

(51) Int. Cl.
*A01H 5/00* (2006.01)

(52) U.S. Cl. ..... Plt./332

(58) Field of Classification Search ..... Plt./332
See application file for complete search history.

*Primary Examiner*—Annette H. Para
*Assistant Examiner*—Susan B McCormick Ewoldt
(74) *Attorney, Agent, or Firm*—C. A. Whealy

(57) ABSTRACT

A new and distinct cultivar of Ivy *Geranium* plant named 'Figradol Purple', characterized by its outwardly spreading and trailing plant habit; freely basal branching habit; freely flowering habit; single red purple-colored flowers; and good garden performance.

2 Drawing Sheets

Botanical designation: *Pelargonium peltatum.*
Cultivar denomination: 'Figradol Purple'.

BACKGROUND OF THE INVENTION

The present invention relates to a new and distinct cultivar of Ivy *Geranium*, botanically known as *Pelargonium peltatum*, and hereinafter referred to by the name 'Figradol Purple'.

The new Ivy *Geranium* plant is a product of a planned breeding program conducted by the Inventor in Saint Malo, France The objective of the breeding program is to create new freely-branching and freely-flowering Ivy *Geranium* cultivars with large flowers and attractive foliage and flower coloration.

The new Ivy *Geranium* plant originated from a cross-pollination made by the Inventor in Saint Malo, France of two unnamed selections of *Pelargonium peltatum*, not patented. The new Ivy *Geranium* was discovered and selected by the Inventor as a flowering plant from within the progeny of the stated cross-pollination in a controlled greenhouse environment in Saint Malo, France.

Asexual reproduction of the new Ivy *Geranium* plant by vegetative terminal cuttings in a controlled greenhouse environment in De Lier, The Netherlands, has shown that the unique features of this new Ivy *Geranium* plant are stable and reproduced true to type in successive generations.

SUMMARY OF THE INVENTION

Plants of the new Ivy *Geranium* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Figradol Purple'. These characteristics in combination distinguish 'Figradol Purple' as a new and distinct cultivar of Ivy *Geranium*:

1. Outwardly spreading and trailing plant habit.
2. Freely basal branching habit.
3. Freely flowering habit.
4. Single red purple-colored flowers.
5. Good garden performance.

Plants of the new Ivy *Geranium* differ primarily from plants of the parent selections in growth habit and plant habit as plants of the new Ivy *Geranium* are more vigorous in growth habit and more uniform in plant habit than plants of the parent selections.

Plants of the new Ivy *Geranium* can be compared to plants of *Pelargonium peltatum* 'Fisblipur', disclosed in U.S. Plant Pat. No. 15,214. In side-by-side comparisons conducted in De Lier, The Netherlands, plants of the new Ivy *Geranium* differed from plants of 'Fisblipur' in the following characteristics:

1. Plants of the new Ivy *Geranium* had a more trailing plant habit than plants of 'Fisblipur'.
2. Flower petals of plants of the new Ivy *Geranium* were more rounded than flower petals of plants of 'Fisblipur'.

Plants of the new Ivy *Geranium* can also be compared to plants of *Pelargonium peltatum* 'Ville de Paris Lilac', not patented. In side-by-side comparisons conducted in De Lier, The Netherlands, plants of the new Ivy *Geranium* differed from plants of 'Ville de Paris Lilac' in the following characteristics:

1. Leaves of plants of the new Ivy *Geranium* were darker in color than leaves of plants of 'Ville de Paris Lilac'.
2. Plants of the new Ivy *Geranium* had larger flowers than plants of 'Ville de Paris Lilac'.

BRIEF DESCRIPTION OF THE PHOTOGRAPHS

The accompanying colored photographs illustrate the overall appearance of the new Ivy *Geranium*, showing the colors as true as it is reasonably possible to obtain in colored reproductions of this type. Colors in the photographs may differ slightly from the color values cited in the detailed botanical description which accurately describe the colors of the new Ivy *Geranium*.

The photograph on the first sheet comprises a side perspective view of a typical flowering plant of 'Figradol Purple' grown in a hanging basket container.

The photograph on the second sheet is a close-up view of a typical inflorescence of 'Figradol Purple'.

DETAILED BOTANICAL DESCRIPTION

The aforementioned photographs and following observations, measurements and values describe plants grown in De Lier, The Netherlands in a glass-covered greenhouse during the spring and under conditions which closely approximate commercial Ivy *Geranium* production. During the production of the plants day temperatures averaged 17° C. and night temperatures ranged from 14° C. to 17° C. Plants had been growing for 15 weeks when the photographs and the description were taken. In the detailed description, color references are made to The Royal Horticultural Society Colour Chart, 2001 Edition, except where general terms of ordinary dictionary significance are used.

Botanical classification: *Pelargonium peltatum* 'Figradol Purple'.

Parentage:

*Female, or seed, parent.*—Unnamed selection of *Pelargonium peltatum*, not patented.

*Male or pollen parent.*—Unnamed selection of *Pelargonium peltatum*, not patented.

Propagation:

*Type.*—By vegetative terminal cuttings.

*Time to initiate roots, summer.*—About four days at temperatures of 22° C.

*Time to initiate roots, winter.*—About one week at temperatures of 22° C.

*Time to produce a rooted young plant, summer.*—About 16 days at temperatures of 22° C. to 30° C.

*Time to produce a rooted young plant, winter.*—About three weeks at temperatures of 20° C. to 25° C.

*Root description.*—Medium in thickness, fibrous; whitish grey in color.

*Rooting habit.*—Freely branching, moderately dense.

Plant description:

*General appearance.*—Outwardly spreading and trailing plant habit; uniformly mounded; densely foliated.

*Growth and branching habit.*—Vigorous growth habit. Freely basal branching habit with about three to five lateral branches per plant.

*Plant height, to top of umbels.*—About 28 cm to 30 cm.

*Plant height, to top of leaves.*—About 18 cm to 25 cm.

*Plant width.*—About 45 cm to 50 cm.

*Lateral branches.*—Length: About 30 cm to 35 cm. Diameter: About 4 mm to 5 mm. Internode length: About 3 cm to 8 cm. Texture: Pubescent. Strength: Strong. Color: Close to 144B.

Foliage description:

*Arrangement.*—Alternate; simple.

*Length.*—About 5 cm to 6.5 cm.

*Width.*—About 9 cm to 10 cm.

*Shape.*—Roughly orbicular; palmately lobed.

*Apex.*—Acute.

*Base.*—Cordate; open.

*Margin.*—Serrate.

*Venation pattern.*—Palmate.

*Texture, upper surface.*—Slightly pubescent.

*Texture, lower surface.*—Smooth, glabrous.

*Color.*—Developing leaves, upper surface: Close to N137D. Developing leaves, lower surface: Close to 137C. Fully developed leaves, upper surface: Close to N137A; venation, close to 144A. Fully developed leaves, lower surface: Close to 137B; venation, close to 144A. Zonation pattern: Intensity: Faint. Width: About 7 mm to 8 mm. Location: About 2 cm from the margin. Color: Close to N189A. Petiole: Length: About 4 cm to 9 cm. Diameter: About 2 mm. Texture, upper and lower surfaces: Smooth, glabrous. Color, upper and lower surfaces: Close to 144A.

Flower description:

*Flower arrangement.*—Single rotate flowers arranged in rounded hemispherical umbels arising from apical leaf axils. Umbels displayed above the foliage on strong peduncles. Flowers face upright to outward; flowers mostly flat.

*Fragrance.*—None detected.

*Quantity of flowers.*—Freely flowering habit; about 19 to 28 flowers and flower buds per umbel.

*Flowering season.*—Year-round under greenhouse conditions. In an outdoor nursery in De Lier, The Netherlands, flowering is continuous from spring until frost in the autumn.

*Flower longevity.*—Individual flowers last about 2 to 14 days on the plant; flowers persistent.

*Umbel height.*—About 8 cm to 9 cm.

*Umbel diameter.*—About 10 cm.

*Flower length.*—About 5 cm to 6 cm.

*Flower width.*—About 5 cm to 5.5 cm.

*Flower depth (height).*—About 2.5 cm.

*Flower buds.*—Length: About 1.5 cm. Diameter: About 5 mm to 6 mm. Shape: Elliptic. Color: Close to 146A.

*Petals.*—Quantity per flower/arrangement: Five in a single whorl. Length: About 2.8 cm. Width: About 1.5 cm. Shape: Spatulate, elongated. Apex: Obtuse. Base: Attenuate. Margin: Entire. Texture, upper and lower surfaces: Smooth, glabrous; velvety. Color: When opening and fully opened, upper surface: Close to N57A; venation, close to N57A. Color becoming closer to N74B with development. When opening and fully opened, lower surface: Close to N57A; venation, close to N57A. Color becoming closer to N74B with development.

*Sepals.*—Quantity per flower/arrangement: Five in a single whorl. Length: About 1.5 cm. Width: About 2 mm to 5 mm. Shape: Lanceolate. Apex: Acute. Base: Cuneate. Margin: Entire. Texture, upper and lower surfaces: Smooth, glabrous. Color, upper surface: Close to N137B. Color, lower surface: Close to N186C.

*Peduncle (umbel stem).*—Length: About 16 cm to 20 cm. Diameter: About 3 mm to 4 mm. Strength: Moderately strong. Angle: Erect to about 30° C. from vertical. Texture: Pubescent. Color: Close to 143B.

*Pedicel (individual flower stem).*—Length: About 3 mm to 3.5 cm. Diameter: About 2 mm. Strength: Moderately strong. Angle: Erect to about 90° C. from vertical. Texture: Pubescent. Color: Close to N186C.

*Reproductive organs.*—Androecium: Stamen quantity per flower: About six to eight. Filament length: About 7 mm. Filament color: Close to 155A. Anther length: About 2 mm. Anther shape: Oblong. Anther color: Close to N77A. Pollen amount: Moderate. Pollen color: Close to 172C. Gynoecium: Pistil quantity per flower: One. Pistil length: About 1.5 cm. Stigma shape: Tapering; reflexed. Stigma color: Close to 187C. Style length: About 3 mm. Style color: Close to 155D. Ovary color: Close to 155D.

*Seed.*—Seed development has not been observed.

Disease/pest resistance: Plants of the new Ivy *Geranium* have not been observed to be resistant to pathogens and pests common to Ivy *Geraniums*.

Garden performance: Plants of the new Ivy *Geranium* have been observed to tolerate rain, wind, and temperatures ranging from about 0° C. to about 45° C. and have demonstrated good garden performance.

It is claimed:

1. A new and distinct Ivy *Geranium* plant named 'Figradol Purple' as illustrated and described.

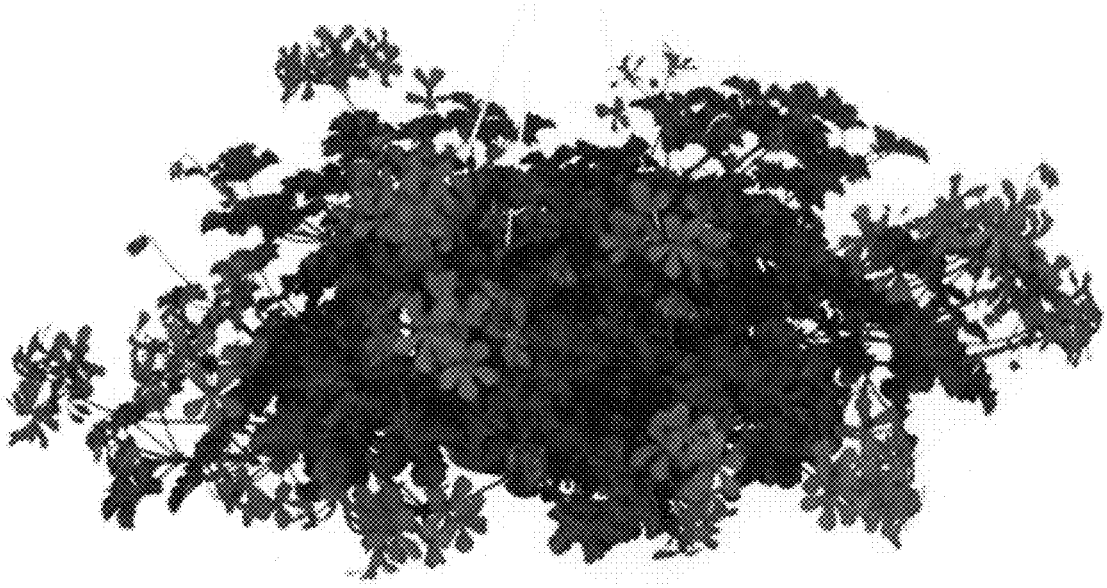

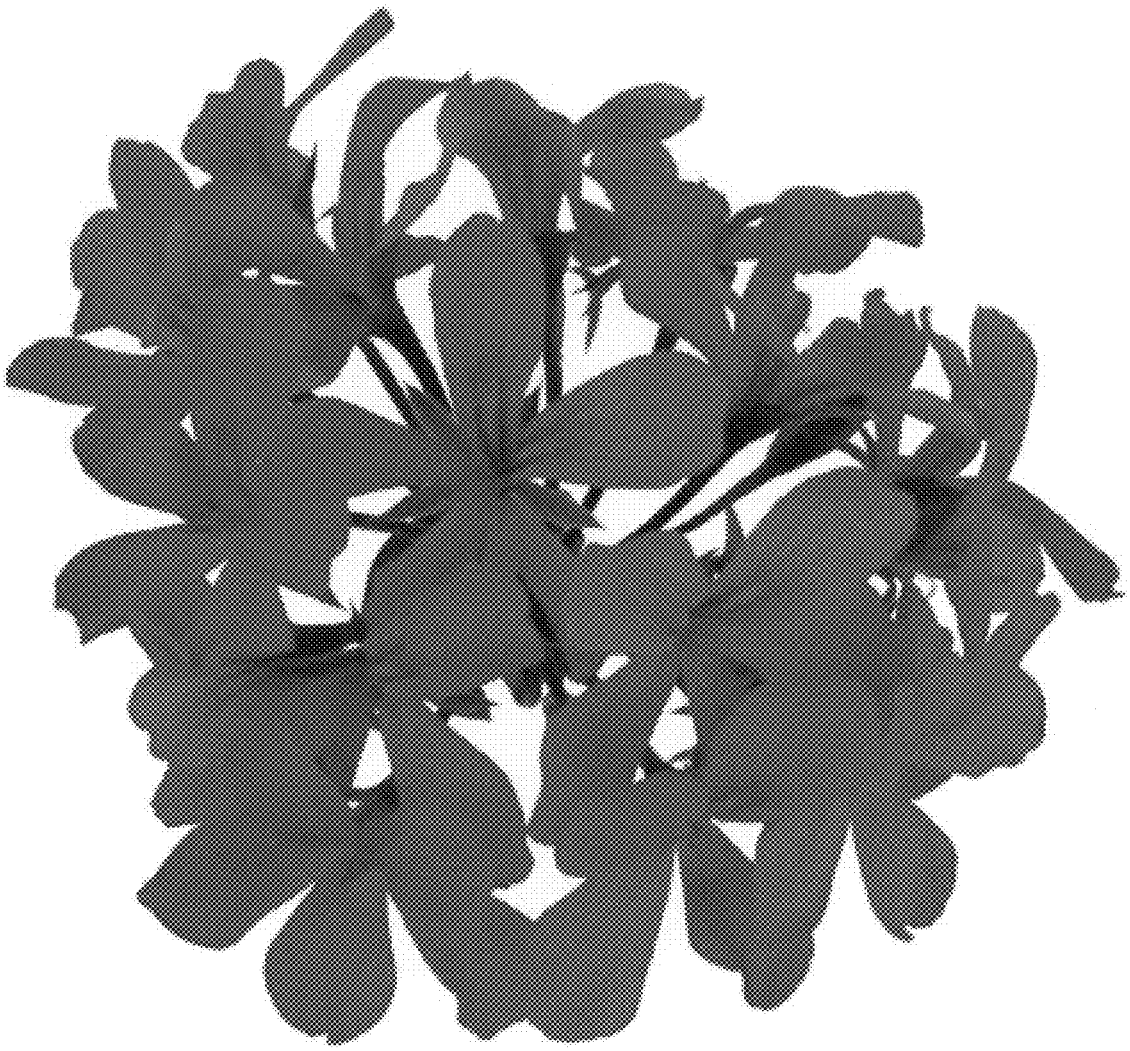

* * * * *